United States Patent [19]

Kodama et al.

[11] Patent Number: 5,853,949
[45] Date of Patent: Dec. 29, 1998

[54] METHOD OF SYNTHESIZING POLYPHENOL COMPOUND AND POSITIVE WORKING PHOTORESIST COMPOSITION COMPRISING POLYPHENOL COMPOUND

[75] Inventors: Kunihiko Kodama; Makoto Momota, both of Shizuoka, Japan

[73] Assignee: Fuji Photo Film Co., Ltd., Kanagawa, Japan

[21] Appl. No.: 657,773

[22] Filed: May 31, 1996

[30] Foreign Application Priority Data

Jun. 2, 1995  [JP]  Japan .................................... 7-136535

[51] Int. Cl.$^6$ ...................................................... G03F 7/023
[52] U.S. Cl. ........................... 430/191; 430/192; 430/193
[58] Field of Search .................................... 430/191, 192, 430/193

[56] References Cited

U.S. PATENT DOCUMENTS

| | | | |
|---|---|---|---|
| 2,839,586 | 6/1958 | Fritz . | |
| 5,178,986 | 1/1993 | Zampini et al. | 430/192 |
| 5,407,779 | 4/1995 | Uetani et al. | 430/191 |
| 5,541,033 | 7/1996 | Blakeney et al. | 430/191 |

FOREIGN PATENT DOCUMENTS

| | | |
|---|---|---|
| 63-83035 | 4/1988 | Japan .............................. C07C 39/15 |
| 908278 | 1/1965 | United Kingdom . |
| 1202762 | 8/1970 | United Kingdom . |
| 1258550 | 12/1971 | United Kingdom . |

*Primary Examiner*—John S. Chu
*Attorney, Agent, or Firm*—Sughrue, Mion, Zinn, Macpeak & Seas, PLLC

[57] ABSTRACT

Provided are a method of synthesizing a highly pure polyphenol compound, which comprises (i) introducing at least one —CHRNR'R" group onto aromatic ring(s) of a phenol compound having from one to ten aromatic ring(s), wherein R represents a hydrogen atom, an alkyl group which may contain a hetero atom, a cycloalkyl group which may contain a hetero atom, an aralkyl group which may contain a hetero atom, or an aryl group, and R' and R", which may be the same or different, each represents an alkyl group which may contain a hetero atom, a cycloalkyl group which may contain a hetero atom, an aralkyl group which may contain a hetero atom, or an aryl group, and R' and R" may combine with each other to form a ring, (ii) converting the —CHRNR'R" group into a —CHRA group via one to three steps, wherein A represents a hydroxyl group, an alkoxy group, an acyloxy group, a halogen atom, a quaternary ammonium salt or a sulfonyloxy group, and (iii) condensing the thus converted phenol compound and a phenol compound, and a positive working photoresist composition using the polyphenol compound obtained by the aforementioned method.

2 Claims, No Drawings

METHOD OF SYNTHESIZING POLYPHENOL COMPOUND AND POSITIVE WORKING PHOTORESIST COMPOSITION COMPRISING POLYPHENOL COMPOUND

FIELD OF THE INVENTION

The present invention relates to a method of synthesizing a polyphenol compound and a positive working photoresist composition prepared by using a polyphenol compound synthesized by the method.

BACKGROUND OF THE INVENTION

Polyphenol compounds are generally applied to various purposes, e.g., positive working photoresist compositions which are used in the process of manufacturing lithographic plates, semiconductor IC and the like, circuit substrates for liquid crystals, thermal heads, etc., and in other photofabrication processes, materials for pressure-sensitive and heat-sensitive papers, raw materials for adhesives, and so on.

As for the syntheses of such polyphenols, the method described in JP-A-63-83035 is known, wherein a trinuclear substituted phenol is synthesized by once isolating a methylol compound obtained by reacting a 4-substituted phenol with an aldehyde in the presence of an alkaline catalyst, and then reacting the isolated methylol compound with an alkyl-substituted phenol in the presence of an acidic catalyst.

However, the polyphenol synthesis according to the above-mentioned method has a problem such that molecules of the methylol compound as an intermediate are liable to react with one another in the presence of an acid or an alkali; as a result, the obtained product contains by-products such as oligomers in fairly large quantities. In addition, the by-products are difficult to separate out. Thus, photoresist compositions using the polyphenols obtained by the known method are still insufficient in performances.

SUMMARY OF THE INVENTION

Therefore, a first object of the present invention is to obtain a polyphenol compound with a reduced quantity of by-products such as olygomers with a simple method and in a high yield.

A second object of the present invention is to obtain a positive working photoresist composition which ensures high resolution and a wide depth of focus by the use of a polyphenol compound with a reduced quantity of by-products.

It has been found that the aforementioned objects of the present invention can be attained with a method of synthesizing a polyphenol compound, which comprises (i) introducing at least one —CHRNR'R" group onto aromatic ring(s) of a phenol compound having from one to ten aromatic ring(s), wherein R represents a hydrogen atom, an alkyl group which may contain a hetero atom, a cycloalkyl group which may contain a hetero atom, an aralkyl group which may contain a hetero atom, or an aryl group, and R' and R", which may be the same or different, each represents an alkyl group which may contain a hetero atom, a cycloalkyl group which may contain a hetero atom, an aralkyl group which may contain a hetero atom, or an aryl group, and R' and R" may combine with each other to form a ring, (ii) converting the —CHRNR'R" group into a —CHRA group via one to three steps, wherein A represents a hydroxyl group, an alkoxy group, an acyloxy group, a halogen atom, a quaternary ammonium salt or a sulfonyloxy group, and (iii) condensing the thus converted phenol compound and a phenol compound.

In the synthesis method of the present invention, the polyphenol compound is synthesized via an aminomethylated compound (a compound containing a —CHRNR'R" group) as an intermediate; as a result, the formation of by-products, such as oligomers, can be inhibited to a very satisfactory extent.

DETAILED DESCRIPTION OF THE INVENTION

In the synthesis method of the present invention, at least one —CHRNR'R" group is firstly introduced into the aromatic ring(s) of a phenol compound having from 1 to 10 aromatic ring(s).

Examples of the phenol compound having from 1 to 10 aromatic ring(s) (Phenol Compound (a)) include those represented by the following formula (I):

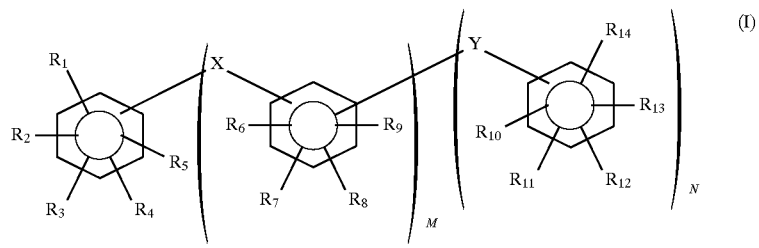

wherein the sum of M and N is an integer of from 0 to 9, preferably from 0 to 7, and more preferably from 1 to 4: X and Y, which may be the same or different, each represents a single bond or a linkage illustrated below;

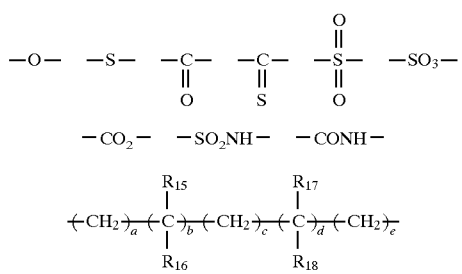

wherein each of a, b, c, d and e represents an integer of from 0 to 4: and $R_1$ to $R_{18}$, which may be the same or different, each represents a hydrogen atom, a halogen atom, an alkyl group, a cycloalkyl group, an aryl group, an alkoxy group, an acyloxy group, an acyl group, an alkenyl group, an aralkyl group, a hydroxyl group or the following group;

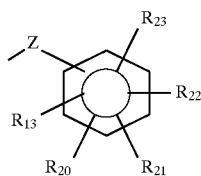

wherein $R_{19}$ to $R_{23}$, which may be the same or different, each represents a hydrogen atom, a halogen atom, an alkyl group, a cycloalkyl group, an aryl group, an alkoxy group, an acyloxy group, an acyl group, an alkenyl group, an aralkyl group or a hydroxyl group, provided that at least one of $R_1$ to $R_{15}$ and $R_{19}$ to $R_{23}$ represents a hydroxyl group, and Z represents a single bond, an alkylene group having 1 to 3 carbon atoms (e.g., methylene, ethylene, propylene, and isopropylene), —O—, —S—,

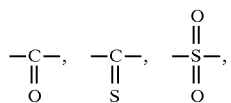

—SO₃—, —CO₂—, —SO₂NH—, or —CONH—.

Examples of the halogen atom include a fluorine atom, a chlorine atom, a bromine atom and an iodine atom, with a chlorine atom and a bromine atoms being preferred. Preferred examples of the alkyl group include a primary alkyl group containing 1 to 6 carbon atoms (e.g., methyl, ethyl, n-propyl, n-butyl and n-hexyl groups), with a methyl group and an ethyl group being more preferred. Preferred examples of the cycloalkyl group include a 3- to 7-membered cycloalkyl group (e.g., cyclopropyl, cyclopentyl and cyclohexyl), with a cyclopentyl group and a cyclohexyl group being more preferred. Preferred examples of the aryl group include those containing 6 to 10 carbon atoms (e.g., phenyl, tolyl, hydroxyphenyl and naphthyl), with a phenyl group and a tolyl group being more preferred. Preferred examples of the alkoxy group include those containing 1 to 4 carbon atoms (e.g., methoxy, ethoxy, propoxy, n-butoxy and 2-methoxy-ethoxy), with a methoxy group, an ethoxy group and a 2-methoxy-ethoxy group are more preferred. Preferred examples of the acyloxy group include those containing 1 to 8 carbon atoms (e.g., acetoxy, propanoyloxy and benzoyloxy), with an acetoxy group and a propanoyloxy group being more preferred. Preferred examples of the acyl group include those containing 1 to 8 carbon atoms (e.g., acetyl, propanoyl, butanoyl and benzoyl), with an acetyl group and a propanoyl group being more preferred. Preferred examples of the alkenyl group include those containing 2 to 4 carbon atoms (e.g., vinyl, propenyl, allyl and butenyl). Preferred examples of the aralkyl group include those containing 7 to 10 carbon atoms (e.g., benzyl and tolylmethyl).

The introduction of a —CHRNR'R" group into the phenol compound (a) can be effected by dissolving the phenol compound (a) into an appropriate solvent and adding thereto a secondary amine compound represented by NHR'R" and an aldehyde represented by RCHO to cause reaction.

R in a —CHRNR'R" group and RCHO represents a hydrogen atom, an alkyl group, a cycloalkyl group, an aralkyl group or an aryl group, which may contain a hetero atom, with a hydrogen atom being most preferred.

R' and R" in —CHRNR'R" group and the amine compound represented by NHR'R", which may be the same or different, each represent an alkyl group, a cycloalkyl group, an aralkyl group or an aryl group, which may contain a hetero atom. Further, R' and R" may combine with each other to form a ring.

The alkyl, cycloalkyl and aralkyl groups represented by R, R' or R" may contain a hetero group.

Examples of the alkyl, cycloalkyl, aralkyl and aryl groups represented by R, R' or R" include the same as those recited with respect to $R_1$ to $R_{23}$ above.

The proportion by mole of a secondary amine compound represented by NHR'R" and an aldehyde represented by RCHO is preferably from 1:0.1 to 1:10, more preferably from 1:0.3 to 1:2, most preferably from 1:0.5 to 1:1.2. The reaction temperature is generally within the range of 0° C. to the reflux temperature of a solvent used, preferably 25° C. to the reflux temperature of a solvent used.

Examples of the solvent include water; solvents of ether type, such as diethyl ether, dipropyl ether, 1,2-dimethoxyethane, diethylene glycol dimethyl ether, tetrahydrofuran, 1,4-dioxane, diisobutyl ether and diphenyl ether; solvents of alcohol type, such as methanol, ethanol, 1-propanol, 2-propanol, 1-butanol, 2-butanol, isobutyl alcohol, 2-methyl-2-propanol, cyclohexanol, ethylene glycol, ethylene glycol monomethyl ether and diethylene glycol; solvents of aromatic hydrocarbon type, such as benzene, toluene, xylene, ethylbenzene and mesitylene; solvents of ketone type, such as acetone, 2-butanone, 3-pentanone, cyclohexanone and methyl isobutyl ketone; solvents of carboxylic acid type, such as acetic acid and propionic acid; solvents of ester type, such as ethyl acetate, γ-butyrolactone, ethyl lactate and ethyl2-ethoxypropionate; solvents of halogenated hydrocarbon type, such as chloroform, dichloromethane, dichloroethane and carbon tetrachloride; solvents of nitrile type, such as acetonitrile and propionitrile; nitro group-containing solvents, such as nitromethane and nitroethane; solvents of amide type, such as N,N-dimethylformamide, N,N-dimethylacetamide, 1,1,3,3-tetramethylurea and N-methylpyrrolidone; solvents of sulfide type, such as carbon disulfide; dimethyl sulfoxide; and so on. These solvents may be used as a mixture of two or more thereof.

Then, the introduced group —CHRNR'R" is converted into a —CHRA group via one to three steps.

A represents a hydroxyl group, an alkoxy group, an acyloxy group, a halogen atom, a quaternary ammonium salt or a sulfonyloxy group.

Preferred examples of the alkoxy group include those containing 1 to 4 carbon atoms (e.g., methoxy, ethoxy, propoxy, n-butoxy and 2-methoxy-ethoxy), with a methoxy group, an ethoxy group and a 2-methoxy-ethoxy group being more preferred.

Preferred examples of the acyloxy group include those containing 1 to 8 carbon atoms (e.g., acetoxy, propanoyloxy and benzoyloxy), with an acetoxy group and a propanoyloxy group being more preferred.

Examples of the halogen atom include a fluorine atom, a chlorine atom, a bromine atom and an iodine atom, with a chlorine atom and a bromine atom being preferred.

Examples of the quaternary ammonium salt include those represented by the formula illustrated below. Ammonium salts substituted with a $C_{1-4}$ alkyl group, a $C_{5-7}$ cycloalkyl group, a $C_{7-10}$ aralkyl group or/and a $C_{6-10}$ aryl group are preferred, and specific examples thereof includes trimethylammonium, ethyldimethylammonium, propyldimethylammonium, n-butyldimethyl-ammonium, phenyldimethylammonium, benzyldimethylammonium and triethylammonium:

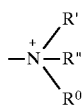

wherein $R^0$ has the same meaning as R'.

Preferred examples of the sulfonyloxy group include those containing 1 to 8 carbon atoms (e.g., methanesulfonyloxy, ethanesulfonyloxy, propanesulfonyloxy, butanesulfonyloxy, benzenesulfonyloxy and toluenesulfonyloxy).

The conversion into a quaternary ammonium salt can be effected by the reaction with an alkyl halide, a carboxylic acid anhydride, a carboxylic acid halide or a sulfonic acid halide in the absence or presence of an appropriate solvent, and if needed, under a heating condition.

The conversion into an acyloxy group can be effected by the reaction with a carboxylic acid anhydride in the absence or presence of an appropriate solvent, or by the reaction of the quaternary ammonium salt obtained above with a carboxylic acid salt and, if necessary, under a heating condition.

The conversion into a hydroxyl group can be effected by hydrolyzing the acyloxy group obtained above in an appropriate solvent in the presence of an acid or alkali catalyst.

The conversion into a halide can be effected by reacting the acyloxy group obtained above with hydrogen halide, or by converting the hydroxide obtained above into the halide.

The conversion into an alkoxy group can be effected by reacting the quaternary ammonium salt obtained above with an alkyl halide in the absence or presence of an appropriate solvent and further reacting with a metal alkoxide, or by reacting the acyloxy compound obtained above with an alcohol in the presence of an alkali catalyst without a solvent or in an appropriate solvent.

The conversion into a sulfonyloxy group can be effected by reacting the hydroxide obtained above with a sulfonic acid halide in an appropriate solvent in the presence of an alkali catalyst.

In the present invention, the polyphenol compound can be synthesized by condensing the phenol compound containing a —CHRA group obtained above and a phenol compound (b).

Examples of the phenol compound (b) include the same phenol compounds as those represented by the foregoing formula (I). The phenol compound (b) to be condensed with the —CHRA group may be the same to or different from the phenol compound (a).

Examples of the phenol compound (b) include phenol, cresols such as m-cresol, p-cresol and o-cresol, xylenols such as 2,5-xylenol, 3,5-xylenol, 3,4-xylenol and 2,3-xylenol, alkylphenols such as m-ethylphenol, p-ethylphenol, o-ethylphenol and p-t-butylphenol, trialkylphenols such as 2,3,5-trimethylphenol and 2,3,4-trimethylphenol, alkoxyphenols such as p-methoxyphenol, m-methoxyphenol, 3,5-dimethoxyphenol, 2-methoxy-4-methylphenol, m-ethoxyphenol, p-ethoxyphenol, m-propoxyphenol, p-propoxyphenol, m-butoxyphenol and p-butoxyphenol, bisalkylphenols such as 2-methyl-4-isopropylphenol, and other hydroxy aromatic compounds such as m-chlorophenol, p-chlorophenol, o-chlorophenol, dihydroxybiphenyl, bisphenol A, phenylphenol, resorcinol and naphthol. These phenols can be used alone or as a mixture of two or more thereof, but it should be understood that those examples are not to be construed as limiting the scope of the invention.

The condensation with a phenol compound (b) can be carried out by reacting the phenol compound containing a —CHRA group with the phenol compound (b) in no solvent or an appropriate solvent in the absence or presence of an acid catalyst.

Although the reaction can be performed in the absence of the catalyst, examples of the acid catalyst include sulfuric acid, hydrochloric acid, nitric acid, carboxylic acids such as acetic acid, trifluoroacetic acid, oxalic acid and formic acid, and sulfonic acids such as p-toluenesulfonic acid and methanesulfonic acid. In the aforesaid condensation reaction, it is preferable to use the phenol compound containing a —CHRA group and the phenol compound (b) at a molar ratio of from 1:1 to 1:100, more preferably from 1:1 to 1:50.

Examples of the solvent used herein include the same solvents as employed in the introduction of the —CHRNR'R" group described above. Two or more of solvents may be used as a mixture thereof.

According to the synthesis method of the present invention, the formation of by-products such as oligomers can be reduced in quantity, and polyphenol compounds can be obtained in a high yield and in the simple manner.

Further, the synthesis method of the present invention can provide polyphenol compounds having sufficiently high purity without a purification step such as column chromatography or recrystallization. However, such a purification step may be taken, if desired, and thereby polyphenol compounds having still higher purity can be obtained.

When the polyphenol compound with small contents of by-products obtained according to the synthesis method of the present invention is applied to a positive working photoresist composition, a positive working photoresist composition having high resolution and wide depth of focus can be obtained.

More specifically, a positive working photoresist composition, comprising an alkali-soluble resin and a naphthoquinone diazide compound, can contain the 1,2-naphthoquinonediazido-5- and/or -4-sulfonic acid ester of the polyphenol compound obtained according to the synthesis method of the present invention as the naphthoquinonediazide compound or the polyphenol compound obtained according to the synthesis method of the present invention as a further component in addition to the alkali-soluble resin and naphthoquinone diazide compound. Further, the positive working photoresist composition may contain both the 1,2-naphthoquinonediazido-5-and/or -4-sulfonic acid ester of the polyphenol compound obtained according to the present invention and the polyphenol compound obtained according to the present invention.

Examples of the alkali-soluble resin which can be used in the positive working photoresist composition include novolak resins, acetone-pyrogallol resins, and polyhydroxystyrene and a derivative thereof.

Of those resins, novolak resins are preferred in particular. The novolak resins are obtained by using prescribed monomers as main constituent, and causing the monomers and aldehydes to undergo addition condensation in the presence of an acid catalyst. Specific examples of the monomer include phenol, cresols such as m-cresol, p-cresol and o-cresol, xylenols such as 2,5-xylenol, 3,5-xylenol, 3,4-xylenol and 2,3-xylenol, alkylphenols such as m-ethylphenol, p-ethylphenol, o-ethylphenol and p-t-butylphenol, trialkylphenols such as 2,3,5-trimethylphenol and 2,3,4-trimethylphenol, alkoxyphenols such as p-methoxyphenol, m-methoxyphenol, 3,5-dimethoxyphenol, 2-methoxy-4-methylphenol, m-ethoxyphenol, p-ethoxyphenol, m-propoxyphenol, p-propoxyphenol, m-butoxyphenol and p-butoxyphenol, bisalkylphenols such as 2-methyl-4-isopropylphenol, and other hydroxy aromatic compounds such as m-chlorophenol, p-chlorophenol, o-chlorophenol, dihydroxybiphenyl, bisphenol A, phenylphenol, resorcinol and naphthol. These phenols can be used alone or as a mixture of two or more thereof, but it should be understood that those examples are not to be construed as limiting the scope of the invention.

Examples of aldehydes include formaldehyde, paraformaldehyde, acetaldehyde, propyl aldehyde, benzaldehyde, phenylacetaldehyde, α-phenylpropyl aldehyde, β-phenylpropyl aldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, p-nitrobenzaldehyde, o-methylbenzaldehyde, m-methylbenzaldehyde, p-methylbenzaldehyde, p-ethylbenzaldehyde, p-n-butylbenzaldehyde, furfural, chloroacetaldehyde, and the acetals thereof such as chloroacetaldehyde diethylacetal. Of these aldehydes, formaldehyde is favored over the others.

The aldehyde can be used alone or as a mixture of two or more thereof.

Examples of the acid catalyst include hydrochloric acid, sulfuric acid, formic acid, acetic acid and oxalic acid.

Further, it is desirable to adopt the arts disclosed, e.g., in JP-A-60-45238, JP-A-60-97347, JP-A-60-140235, JP-A-60-189739, JP-A-64-14229, JP-A-01-276131, JP-A-02-60915, JP-A-02-275955, JP-A-02-282745, JP-A-04-101147 and JP-A-04-122938, that is, the arts of removing or reducing low molecular weight components of novolak resins.

The weight average molecular weight of the thus obtained novolak resins is preferably within the range of 2,000 to 20,000, more preferably 3,000 to 15,000. When it is less than 2,000, a great decrease in resist film thickness in the unexposed area is caused after development; while when it is more than 20,000, the development rate becomes slow. The term "weight average molecular weight" as used herein is defined as the value reduced to polystyrene by gel permeation chromatography.

The dispersibility of those resins (the ratio of the weight average molecular weight Mw to the number average molecular weight Mn, or Mw/Mn) is preferably from 1.5 to 7.0, and more preferably from 1.5 to 4.0. When the dispersibility is greater than 7.0, there is a possibility that the effects of the present invention cannot be achieved to a satisfactory extent. When the dispersibility is smaller than 1.5, on the other hand, the synthesis of such novolak resins may require a high level of purification step, and so it is unsuitable from a practical point of view.

As for the photosensitive material of a positive working photoresist composition, a naphthoquinone diazide compound is used. Specific examples of such a naphthoquinone diazide compound include not only the products of esterification reaction of the polyphenol compounds obtained by the synthesis method of the present invention with 1,2-naphthoquinonediazido-5-(and/or -4-)sulfonyl chloride but also the products of esterification reaction of other polyphenol compounds as cited below with 1,2-naphthoquinonediazido-5-(and/or -4-)sulfonyl chloride. The former esterification reaction products and the latter may be used in combination.

As examples of a polyphenol compound other than those prepared according to the present invention, mention may be made of polyhydroxybenzophenones, such as 2,3,4-trihydroxybenzophenone, 2,4,4'-trihydroxybenzophenone, 2,4,6-trihydroxybenzophenone, 2,3,4-trihydroxy-2'-methylbenzophenone, 2,3,4,4'-tetrahydroxybenzophenone, 2,2',4,4'-tetrahydroxybenzophenone, 2,4,6,3',4'-pentahydroxybenzophenone, 2,3,4,2',4'-pentahydroxybenzophenone, 2,3,4,2',5'-pentahydroxybenzophenone, 2,4,6,3',4',5'-hexahydroxybenzophenone and 2,3,4,3',4',5'-hexahydroxybenzophenone; polyhydroxyphenylalkyl ketones, such as 2,3,4-trihydroxyacetophenone, 2,3,4-trihydroxyphenylpentyl ketone and 2,3,4-trihydroxyphenylhexyl ketone; bis((poly)hydroxyphenyl) alkanes, such as bis(2,4-dihydroxyphenyl) methane, bis(2,3,4-trihydroxyphenyl)methane, bis(2,4-dihydroxyphenyl) propane-1, bis(2,3,4-trihydroxyphenyl)propane-1, nordihydroguaiaretic acid and 1,1-bis (4-hydroxyphenyl) cyclohexane; polyhydroxybenzoic acid esters, such as propyl 3,4,5-trihydroxybenzoate, phenyl 2,3,4-trihydroxybenzoate and phenyl 3,4,5-trihydroxybenzoate; bis(polyhydroxybenzoyl)alkanes or bis (polyhydroxybenzoyl)arenes, such as bis(2,3,4-trihydroxybenzoyl)methane, bis(3-acetyl-4,5,6-trihydroxyphenyl)methane, bis(2,3,4-trihydroxybenzoyl) benzene and bis(2,4,6-trihydroxybenzoyl)benzene; alkylene -di(polyhydroxybenzoate)s, such as ethylene glycol di(3,5-dihydroxybenzoate) and ethylene glycol di(3,4,5-trihydroxybenzoate); polyhydroxybiphenyls, such as 2,3,4-biphenyltriol, 3,4,5-biphenyltriol, 3,5,3',5'-biphenyltetrol, 2,4,2',4'-biphenyltetrol, 2,4,6,3',5'-biphenylpentol, 2,4,6,2', 4',6'-biphenylhexol and 2,3,4,2',3',4'-biphenylhexol; bis (polyhydroxy)sulfides, such as 4,4'-thiobis(1,3-dihydroxy) benzene; bis(polyhydroxyphenyl)ethers, such as 2,2',4,4'-tetrahydroxydiphenyl ether; bis(polyhydroxyphenyl) sulfoxides, such as 2,2',4,4'-tetrahydroxydiphenyl sulfoxide; bis(polyhydroxyphenyl)sulfones, such as 2,2',4,4'-diphenylsulfone; polyhydroxytriphenyl methanes, such as tris(4-hydroxyphenyl)methane, 4,4',4"-trihydroxy-3,5,3',5'-tetramethyltriphenylmethane, 4,4',3",4"-tetrahydroxy-3,5,3', 5'-tetramethyltriphenylmethane, 4-[bis(3,5-dimethyl-4-hydroxyphenyl)methyl]-2-methoxy-phenol, 4,4'-(3,4-diolbenzylidene)bis[2,6-dimethylphenol], 4,4'-[(2-hydroxyphenyl)methylene]bis[2-cyclohexyl-5-methylphenol], 4,4',2",3",4"-pentahydroxy-3,5,3',5'-tetramethyltriphenylmethane, 2,3,4,2',3',4'-hexahydroxy-5, 5'-diacetyltriphenylmethane, 2,3,4,2',3',4',3",4"-octahydroxy-5,5'-diacetyltriphenylmethane and 2,4,6,2',4', 6'-hexahydroxy -5,5'-dipropionyltriphenylmethane; polyhydroxytriphenylethanes, such as 4,4'-(phenylmethylene)bisphenol, 4,4'-(1-phenyl ethylidene)bis [2-methylphenol] and 4,4',4"-ethylidenetrisphenol; polyhydroxyspirobi-indanes, such as 3,3,3',3'-tetramethyl-1, 1'-spirobi-indane-5,6,5',6'-tetrol, 3,3,3',3'-tetramethyl-1,1'-spirobi-indane-5,6,7,5',6',7'-hexol, 3,3,3',3'-tetramethyl-1,1'-spirobi-indane-4,5,6,4',5',6'-hexol and 3,3,3',3'-tetramethyl-1,1'-spirobi-indane-4,5,6,5',6',7'-hexol, polyhydroxyflavans, such as 2,4,4-trimethyl-2',4',7'-trihydroxyflavan; polyhydroxyphthalides, such as 3,3-bis(3,4-dihydroxyphenyl)phthalide, 3,3-bis(2,3,4-trihydroxyphenyl) -phthalide and 3',4',5',6'-tetrahydroxyspiro[phthalide-3,9'-xanthene]; flavonoid such as morin, quercetin and rutin; the polyphenol compounds described in JP-A-04-253058, such as α,α',α"-tris(4-hydroxyphenyl) 1,3,5-triisopropylbenzene, α,α',α"-tris(3,5-dimethyl-4-hydroxyphenyl) 1,3,5-triisopropylbenzene, α,α', α"-tris(3,5-diethyl-4-hydroxyphenyl) 1,3,5-triisopropylbenzene, α,α',α"-tris(3,5-di-n-propyl-4-hydroxyphenyl) 1,3,5-triisopropylbenzene, α,α',α"-tris(3,5-diisopropyl-4-hydroxyphenyl) 1,3,5-triisopropylbenzene, α,α',α"-tris(3,5-di-n-butyl-4-hydroxyphenyl) 1,3,5-triisopropylbenzene, α,α',α"-tris(3-methyl-4-hydroxyphenyl) 1,3,5-triisopropylbenzene, α,α',α"-tris(3- methoxy-4-hydroxyphenyl) 1,3,5-triisopropylbenzene, α,α', α"-tris(2,4-dihydroxyphenyl) 1,3,5-triisopropylbenzene, 1,3,5-tris(3,5-dimethyl-4-hydroxyphenyl)benzene, 1,3,5-tris (5-methyl-2-hydroxyphenyl)benzene, 2,4,6-tris(3,5-dimethyl-4-hydroxyphenylthiomethyl)mesitylene, 1-[α-methyl-α-(4'-hydroxyphenyl) ethyl]-4-[α,α'-bis (4"-hydroxyphenyl) -ethyl]benzene, 1-[α-methyl-α-(4'-hydroxyphenyl)ethyl]-3-[α,α'-bis(4"-hydroxyphenyl)ethyl] benzene, 1-[α-methyl-α-(3',5'-dimethyl-4'-hydroxyphenyl) ethyl]-4-[α,α'-bis(3",5"-dimethyl-4"-hydroxyphenyl)ethyl] benzene, 1-[α-methyl-α-(3'-methyl-4'-hydroxyphenyl) ethyl]-4-[α',α'-bis(3"-methyl-4"-hydroxyphenyl)ethyl] benzene, 1-[α-methyl-α-(3'-methoxy-4'-hydroxyphenyl) ethyl]-4-[α',α'-bis(3"-methoxy-4"-hydroxyphenyl)ethyl] benzene, 1-[α-methyl-α-(2',4'-dihydroxyphenyl)ethyl]-4-[α',α'-bis(4"-hydroxyphenyl)ethyl]benzene and 1-[α-methyl-α-(2',4'-dihydroxyphenyl)ethyl]-3- [α',α'- bis(4"-hydroxyphenyl)ethyl]benzene; the polyphenol compounds described in JP-A-05-224410 such as α,α,α',α',α",α"-hexakis-(4-hydroxyphenyl)-1,3,5-triethylbenzene, and the poly(hydroxyphenyl)alkanes described in JP-A-05-303200 and EP -530148, such as 1,2,2,3-tetra(p-hydroxyphenyl) propane and 1,3,3,5-tetra(p-hydroxyphenyl)pentane; and other polyphenol compounds, such as p-bis(2,3,4-trihydroxybenzoyl)benzene, p-bis (2,4,6-trihydroxybenzoyl)benzene, m-bis(2,3,4-trihydroxybenzoyl)benzene, m-bis(2,4,6-trihydroxybenzoyl) -benzene, p-bis(2,5-dihydroxy-3-bromobenzoyl)benzene, p-bis (2,3,4-trihydroxy-5-methylbenzoyl)benzene, p-bis(2,3,4-trihydroxy-5-methoxybenzoyl)benzene, p-bis(2,3,4-trihydroxy-5-nitrobenzoyl)benzene, p-bis(2,3,4-trihydroxy-5-cyanobenzoyl) -benzene, 1,3,5-tris(2,5-dihydroxybenzoyl) benzene, 1,3,5-tris(2,3,4-trihydroxybenzoyl)benzene, 1,2,3-tris(2,3,4-trihydroxybenzoyl)benzene, 1,2,4-tris(2,3,4-trihydroxybenzoyl)benzene, 1,2,4,5-tetrakis(2,3,4-trihydroxybenzoyl)benzene, α,α'-bis(2,3,4-trihydroxybenzoyl)-p-xylene, α,α',α'-tris(2,3,4-trihydroxybenzoyl)mesitylene, 2,6-bis(2-hydroxy-3,5-dimethylbenzyl) 2,6-bis(2-hydroxy -5'-methylbenzyl)-p-cresol, 2,6-bis(2,4,6-trihydroxybenzyl)-p-cresol, 2,6-bis(2,3,4-trihydroxybenzyl)-p-cresol, 2,6-bis(2,3,4-trihydroxybenzyl)-3,5-dimethylphenol, 4,6-bis(4-hydroxy-3,5-dimethylbenzyl)pyrogallol, 2,6-bis(4-hydroxy-3,5-dimethylbenzyl)-1,3,4-trihydroxyphenol, 4,6-bis(2,4,6-trihydroxybenzyl)-2,4-dimethylphenol, 4,6-bis(2,3,4-trihydroxybenzyl)-2,5-dimethylphenol, 2,6-bis(4-hydroxybenzyl) -p-cresol, 2,6-bis(4-hydroxybenzyl)-4-cyclohexylphenol, 2,6-bis(4-hydroxy-3-methylbenzyl)-p-cresol, 2,6-bis(4-hydroxy-3,5-dimethylbenzyl)-p-cresol, 2,6-bis(4-hydroxy-2,5-dimethylbenzyl)-p-cresol, 2,6-bis(4-hydroxy-3-methylbenzyl)-4-phenylphenol, 2,2',6,6'-tetrakis [(4-hydroxyphenyl)methyl]-4,4'-methylenediphenol, 2,2',6, 6'-tetrakis[(4-hydroxy-3,5-dimethylphenyl)methyl]-4,4'-methylenediphenol, 2,2',6,6'-tetrakis[(4-hydroxy-3-methylphenyl)methyl]-4,4'-methylenediphenol and 2,2'-bis[ (4-hydroxy-3,5-dimethylphenyl)methyl]-6,6'-dimethyl-4,4'-methylenediphenol.

The esterification reaction for obtaining the photosensitive material described above is achieved by dissolving the foregoing polyphenol compound and 1,2-naphthoquinonediazido-5-(and/or -4-)sulfonyl chloride in a solvent each in a prescribed amount. Examples of the solvent include dioxane, acetone, tetrahydrofuran, methyl ethyl ketone, N-methylpyrrolidone, chloroform, trichloroethane, trichloroethylene or dichloroethane, and conducting condensation therein by adding dropwise thereto a basic catalyst, such as sodium hydroxide, sodium carbonate, sodium hydrogen carbonate, triethylamine, N-methylmorpholine, N-methylpiperazine or 4-dimethylaminopyridine. The thus obtained product is washed with water, purified, and then dried.

In a general esterification reaction, the product obtained is a mixture of esterified compounds differing in esterification number and esterified site. However, it is also possible to selectively prepare some particular isomer alone by choosing the reaction condition and the structure of a polyphenol compound to be esterified. The term "esterification rate" as used in the present invention refers to the average of esterification rates of the aforesaid mixture.

Such an esterification rate can be controlled by properly choosing the ratio between starting materials to be mixed, namely a polyphenol compound and 1,2-naphthoquinonediazido-5-(and/or -4-)sulfonyl chloride. More specifically, since substantially all the 1,2-naphthoquinonediazido-5-(and/or -4-)sulfonyl chloride added undergoes the esterification reaction, a mixture having a desired esterification rate can be obtained by adjusting the molar ratio between the starting materials.

1,2-Naphthoquinonediazido-5-sulfonyl chloride and 1,2-naphthoquinonediazido-4-sulfonyl chloride may be used together, if desired.

The reaction temperature in the foregoing method is generally from −20° C. to 60° C., and preferably from 0° to 40° C.

In the photoresist composition, the photosensitive material prepared according to the present invention is mixed with an alkali-soluble resin. The photosensitive material may be used singly or as a mixture of two or more thereof. The amount of the photosensitive material is generally from 5 to 100 parts by weight, preferably from 20 to 60 parts by weight, per 100 parts by weight of the amount of the alkali-soluble resin. When it is less than 5 parts by weight, the remaining rate of resist film is considerably low; while it exceeds 100 parts by weight, the sensitivity and the solubility in a solvent is lowered.

In the photoresist composition of the present invention, a polyphenol compound can further be used for the purpose of promoting the dissolution in a developer. Examples of such a polyphenol compound include polyphenol compounds as set forth below as well as the polyphenol compounds obtained according to the present invention.

As examples of a polyphenol compound suitable for the aforesaid purpose, mention may be made of phenols, resorcinol, phloroglucinol, 2,3,4-trihydroxybenzophenone, 2,3,4,4'-tetrahydroxybenzophenone, 2,3,4,3',4',5'-hexahydroxybenzophenone, acetone-pyrogallol condensed resin, phloroglucidol, 2,4,2',4'-biphenyltetrol, 4,4'-thiobis(1, 3-dihydroxy)benzene, 2,2',4,4'-tetrahydroxydiphenyl ether, 2,2',4,4'-tetrahydroxydiphenyl sulfoxide, 2,2',4,4'-tetrahydroxydiphenyl sulfone, tris(4-hydroxyphenyl) methane, 1,1-bis(4-hydroxyphenyl)cyclohexane, 4,4'-(α-methylbenzylidene)bisphenol, α,α',α"-tris(4-hydroxyphenyl) -1,3,5-triisopropylbenzene, α,α',α"-tris(4-hydroxyphenyl)-1-ethyl-4-isopropylbenzene, 1,2,2-tris (hydroxyphenyl)propane, 1,1,2-tris(3,5-dimethyl-4-hydroxyphenyl)propane, 2,2,5,5-tetrakis(4-hydroxyphenyl) hexane, 1,2-tetrakis(4-hydroxyphenyl)ethane, 1,1,3-tris (hydroxyphenyl)butane and para[α,α,α',α-tetrakis(4-hydroxyphenyl)]xylene.

The polyphenol compound can be mixed generally in a proportion of not greater than 100 parts by weight, preferably from 5 to 50 parts by weight, per 100 parts by weight of the quinonediazide compound.

Examples of a solvent which can be used for dissolving the photosensitive material and an alkali-soluble resin include ethylene glycol monomethyl ether, ethylene glycol monoethyl ether, methyl cellosolve acetate, ethyl cellosolve acetate, diethylene glycol monomethyl ether, diethylene glycol monoethyl ether, propylene glycol methyl ether acetate, propylene glycol propyl ether acetate, propylene glycol monomethyl ether propionate, toluene, xylene, methyl ethyl ketone, cyclopentanone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl β-methoxyisobutyrate, methyl α-hydroxyisobutyrate, methyl pyruvate, ethyl acetate, and butyl acetate. These organic solvents are used alone or as a mixture of two or more thereof.

Also, the organic solvent cited above can be used in combination with a high boiling point solvent, such as N-methylformamide, N,N-dimethylformamide, N-methylacetamide, N,N-dimethylacetamide, N-methylpyrrolidone, dimethyl sulfoxide and benzyl ethyl ether.

The positive working photoresist composition may contain a surfactant in order to improve upon coating properties such as striation.

As examples of the surfactant, mention may be made of nonionic surfactants including polyoxyethylene alkyl ethers, such as polyoxyethylene lauryl ether, polyoxyethylene stearyl ether, polyoxyethylene cetyl ether and polyoxyethylene oleyl ether; polyoxyethylene alkyl allyl ethers, such as polyoxyethylene octyl phenol ether and polyoxyethylene nonyl phenol ether; polyoxyethylene-polyoxypropylene block copolymers; sorbitan fatty acid esters, such as sorbitan monolaurate, sorbitan monopalmitate, sorbitan monostearate, sorbitan monooleate, sorbitan trioleate and sorbitan tristearate; and polyoxyethylenesorbitan fatty acid esters, such as polyoxyethylenesorbitan monolaurate, polyoxyethylenesorbitan monopalmitate, polyoxyethylenesorbitan monostearate, polyoxyethylenesorbitan trioleate and polyoxyethylenesorbitan tristearate: fluorine-containing surfactants, such as EFTOP EF 301, EF303 and EF352 (trade names, products of Shin Akita Kasei Co., Ltd.), Megafac F171 and F173 (trade names, products of Dai-Nippon Ink & Chemicals Inc.), Florade FC430 and FC431 (trade names, products of Sumitomo 3M), and Asahi Guard AG710, Surflon S-382, SC101, SC102, SC103, SC104, SC105 and SC106 (trade names, products of Asahi Glass Company Ltd.): organosiloxane polymers, such as KP341 (code name, a product of Shin-Etsu Chemical Co., Ltd.): and acrylic acid or methacrylic acid (co)polymers, such as Polyflow No. 75 and No. 95 (trade name, products of Kyoeisha Yushi Kagaku Kogyo K.K.). Of these surfactants, a fluorine type and silicone type surfactant are preferred. The amount of the surfactant is generally 2 parts by weight or less, preferably 1 part by weight or less, per 100 parts by weight of the total of the alkali-soluble resin and the quinonediazide compound contained in the composition.

The surfactant may be added alone or as a mixture of two or more thereof.

Examples of the developing solution which can be used for the positive working photoresist composition of the present invention include an aqueous solution of alkali such as inorganic alkalis (e.g., sodium hydroxide, potassium hydroxide, sodium carbonate, sodium silicate, sodium metasilicate and aqueous ammonia), primary amines (e.g., ethylamine and n-propylamine), secondary amines (e.g., diethylamine and di-n-butylamine), tertiary amines (e.g., triethylamine and methyldiethylamine), alcohol amines (e.g., dimethylethanolamine and triethanolamine), quaternary ammonium salts (e.g., tetramethylammonium hydroxide, tetraethylammonium hydroxide and choline), and cyclic amines (e.g., pyrrole and piperidine). Also, an alcohol (e.g., isopropyl alcohol) and/or a surfactant (e.g., a nonionic type surfactant) may be added in an appropriate amount into the aqueous solution of alkali.

Of those developing solutions, an aqueous solution of quaternary ammonium salts is preferred, and tetramethylammonium hydroxide and choline are more preferred.

The positive working photoresist composition of the present invention can contain a light absorbent, a crosslinking agent, an adhesion assistant and so on, if needed.

The light absorbent is added for the purpose of inhibiting halation from a substrate or enhancing perceptibility when the photoresist composition is coated on a transparent support, if needed. Suitable examples of such a light absorbent include commercially available ones as described, e.g., in *Koqyo-yo Shikiso no Gijutsu to Shijo* (which means "Arts and Market of Industrial Dyes") published by CMC Shuppan ann *Senryo Binran* (which means "Handbook of Dyes") compiled by Yuki Gosei Kagaku Kyokai, such as C.I. Disperse Yellow 1, 3, 4, 5, 7, 8, 13, 23, 31, 49, 50, 51, 54, 56, 60, 64, 66, 68, 79, 82, 88, 90, 93, 102, 114 and 124, C.I. Disperse Orange 1, 5, 13, 25, 29, 30, 31, 44, 57, 72 and 73, C.I. Disperse Red 1, 5, 7, 13, 17, 19, 43, 50, 54, 58, 65, 72, 73, 88, 117, 137, 143, 199 and 210, C.I. Disperse Violet 43, C.I. Disperse Blue 96, C.I. Fluorescent Brightening Agent 112, 135 and 165, C.I. Solvent Yellow 14, 16, 33 and 56, C.I. Solvent Orange 2 and 45, C.I. Solvent Red 1, 3, 8, 23, 24, 25, 27 and 49, and C.I. Pigment Green 10, C.I. Pigment Brown 2. The light absorbent is blended generally in a proportion of not greater than 100 parts by weight, preferably not greater than 50 parts by weight, and more preferably not greater than 30 parts by weight, per 100 parts by weight of the alkali-soluble resin.

The crosslinking agent can be added to such an extent that the addition does affect the formation of a positive image. The purpose of the addition of the crosslinking agent resides in improvements of sensitivity adjustment, heat resistance, and dry etching resistance.

Examples of the crosslinking agent include compounds obtained by acting formaldehyde on melamine, benzoguanamine, glycoluril and the like, alkyl-modified compounds thereof, epoxy compounds, aldehydes, azide compounds, organic peroxides, and hexamethylenetetramine. The crosslinking agent can be blended generally in a proportion of less than 10 parts by weight, preferably less than 5 parts by weight, per 100 parts by weight of the photosensitive material. The addition of the crosslinking agent in an amount of more than 10 parts by weight is undesirable since a drop in sensitivity and generation of scum (resist residue) may be caused.

The adhesion assistant is added for the purpose of heightening the adhesiveness of the resist to a substrate, thereby preventing the resist from peeling off, particularly in an etching step. Examples thereof include chlorosilanes, such as trimethylchlorosilane, dimethylvinylchlorosilane, methyldiphenylchlorosilane and chloromethyldimethylchlorosilane; alkoxysilanes, such as trimethylmethoxysilane, dimethyldiethoxysilane, methyldimethoxysilane, dimethylvinylethoxysilane, diphenyldimethoxysilane and phenyltriethoxysilane; silazanes, such as hexamethyldisilazane, N,N'-bis(trimethylsilyl)urea, dimethyltrimethylsilylamine and trimethylsilylimidazole; silanes, such as vinyltrichlorosilane, γ-chloropropyltrimethoxysilane, γ-aminopropyltriethoxysilane and γ-glycidoxypropyltrimethoxysilane; heterocyclic compounds, such as benzotriazole, benzimidazole, indazole, imidazole, 2-mercaptobenzimidazole, 2-mercaptobenzothiazole, 2-mercaptobenzoxazole, urazole, thiouracil, mercaptoimidazole and mercaptopyrimidine; and urea compounds, such as 1,1-dimethylurea and 1,3-dimethylurea, or thiourea compounds.

The adhesion assistant is blended generally in a proportion of less than 10 parts by weight, preferably less than 5 parts by weight, per 100 parts by weight of the alkali-soluble resin.

The positive working photoresist composition is coated on a substrate for production of precision integrated circuit elements (e.g., a transparent substrate such as silicon/silicon dioxide-coated, glass substrate and ITO substrate) by an appropriate coating means such as a spinner or coater. The coated composition is subjected successively to prebake, exposure to light via a desired mask, and, if needed, PEB (PEB: Post Exposure Bake), and then subjected to development, rinsing and drying to provide a satisfactory resist.

The present invention will now be illustrated in more detail by reference to the following examples.

SYNTHESIS EXAMPLE 1 [Synthesis of Compound (4)]

Synthesis of Compound (4) was carried out in accordance with a reaction scheme illustrated below:

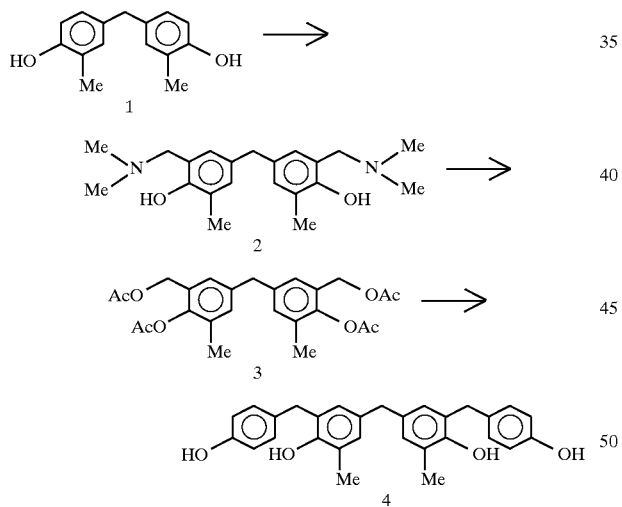

More specifically, 20 g of Compound (1), 79 g of a 50% aqueous solution of dimethylamine and 69 g of a 37% aqueous solution of formaldehyde were dissolved in 150 ml of ethanol, and heated under reflux for 5 hours. The resultant solution was poured into 2 l of water, and the viscous matter obtained was washed with water and then dried. Thus, 27.6 g of Compound (2) was obtained.

27.6 g of Compound (2) was dissolved in 150 ml of acetic anhydride, and heated under reflux for 10 hours. The solvent was distilled away under reduced pressure, and thereby 35.7 g of Compound (3) was obtained.

35.7 g of Compound (3) and 147 g of phenol were dissolved in 150 ml of methanol, and thereto was added 0.77 g of sulfuric acid. Then, the solution was heated under reflux for 5 hours. The resultant solution was poured into 2 l of water. The thus obtained viscous solid was washed with water and then dried. Thus, 31.0 g of a product (4a) comprising Compound (4) and its isomers was obtained. The oligomer content in the product was proved to be 8.5% by a gel permeation chromatography (GPC) measurement.

The oligomer content was determined as follows: The molecular weight distribution in the product was examined by GPC defined in terms of the standard polystyrene as reference value. For the measurement, an ultraviolet light having a wavelength of 282 nm was used. The area of a pattern region corresponding to molecular weights higher than that of the intended compound was determined. The oligomer content was defined as the proportion of area to the entire pattern area. This definition is applied in the following synthesis examples as well.

SYNTHESIS EXAMPLE 2 [Synthesis of Compound (9)]

Synthesis of Compound (9) was carried out in accordance with a reaction scheme illustrated below:

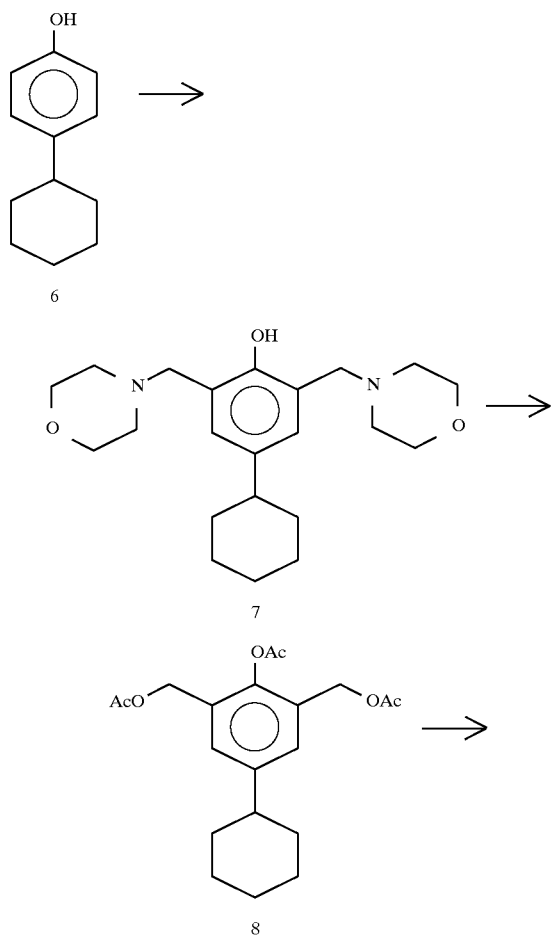

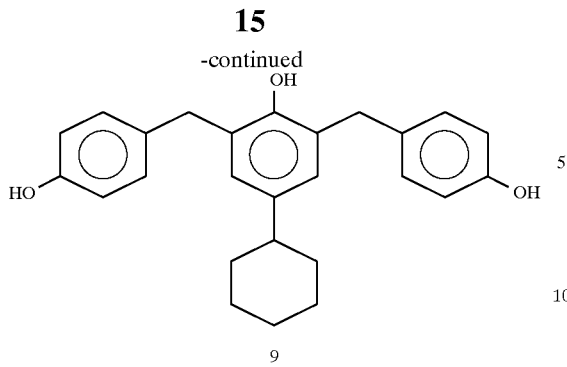

9

30 g of 4-cyclohexylphenol (Compound (6)) was dissolved in 300 ml of ethanol, and 150 g of morpholine was added thereto. Into this solution, 135 g of a 37% aqueous solution of formaldehyde was dripped over 30 minutes. Therein, the reaction was conducted for 8 hours under reflux temperature. The resultant solution was poured into 2 l of water, and the viscous matter obtained was washed with water, followed by drying. Thus, 48.3 g of Compound (7) was obtained.

48.3 g of Compound (7) was admixed with 224 g of acetic anhydride, and the reaction was conducted for 30 hours under reflux temperature. From the resultant solution, unreacted acetic anhydride was distilled away. Thus, 53.1 g of Compound (8) was obtained.

In 300 ml of methanol, 50 g of Compound (8) and 260 g of phenol were dissolved. To this solution was added 1.35 g of concentrated sulfuric acid, and therein the reaction was conducted for 8 hours under reflux temperature. The resultant solution was poured into 5 l of water, and the viscous matter obtained was washed with 3 l of water and then dried. Thus, 47 g of a product (9a) comprising Compound (9) and its isomers was obtained. From the measurement by GPC, the oligomer content in the product was evaluated to be 6.8%.

SYNTHESIS EXAMPLE 3 [Synthesis of Compound (13)]

Synthesis of Compound (13) was carried out in accordance with a reaction scheme illustrated below:

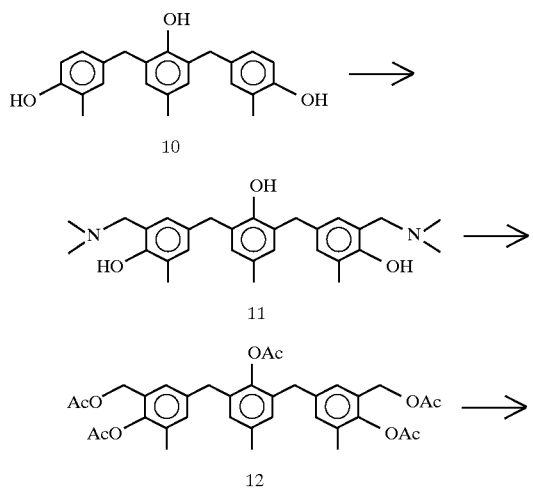

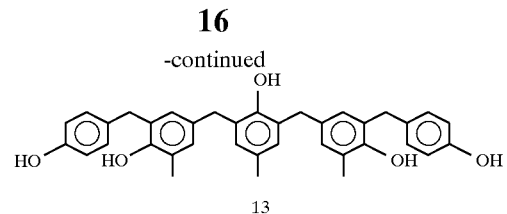

13

More specifically, 10 g of Compound (10) and 26 g of a 50% aqueous solution of dimethylamine were dissolved in 50 ml of ethanol. Thereto, 23 g of a 37% aqueous solution of formaldehyde was added dropwise over 30 minutes, and heated under reflux for 5 hours. The resultant solution was poured into 1 l of water, and the crystals obtained were washed with water and then dried. Thus, 12.4 g of Compound (11) was obtained.

12.4 g of Compound (11) was dissolved in 7 ml of acetic anhydride, and heated under reflux for 10 hours. The solvent was distilled away under reduced pressure to thereby obtain 16.1 g of Compound (12).

16.1 g of Compound (12) and 49 g of phenol were dissolved in 80 ml of methanol, and thereto was added 0.26 g of sulfuric acid. Then, the solution was heated under reflux for 5 hours. The resultant solution was poured into 2 l of water. The thus obtained viscous solid was washed with water and then dried. Thus, 12.4 g of a product comprising Compound (13) and its isomers was obtained. The GPC measurement proved that the oligomer content in the product was 8.5%.

SYNTHESIS EXAMPLE 4 [Synthesis of Compound (17)]

Synthesis of Compound (17) was carried out in accordance with a reaction scheme illustrated below:

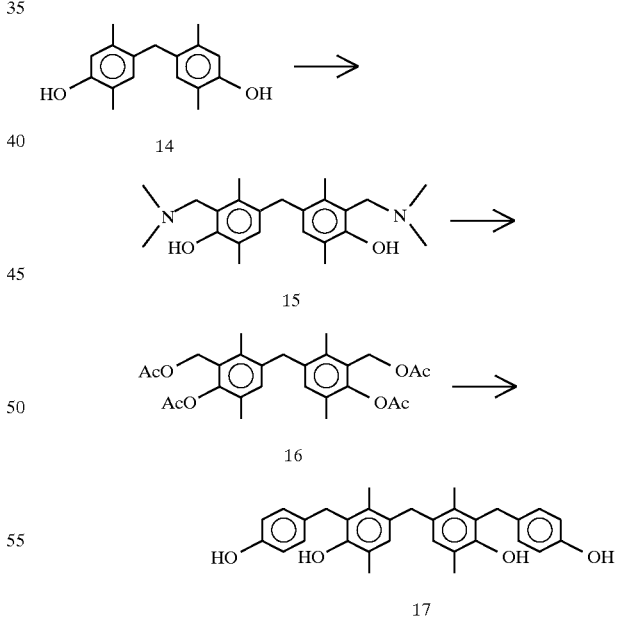

20 g of Compound (14) and 70 g of a 50% aqueous solution of dimethylamine were dissolved in 150 ml of ethanol. Thereto, 61 g of a 37% aqueous solution of formaldehyde was added dropwise over 30 minutes, and heated under reflux for 5 hours. The resultant solution was poured into 2 l of water, and the crystals obtained were washed with water and then dried. Thus, 27.5 g of Compound (15) was obtained.

27.5 g of Compound (15) was dissolved in 150 ml of acetic anhydride, and heated under reflux for 10 hours. The solvent was distilled away under reduced pressure, and the powder obtained was washed with water, followed by drying. Thus, 32.2 g of Compound (16) was obtained.

32.2 g of Compound (16) and 125 g of phenol were dissolved in 150 ml of methanol, and thereto was added 13.1 g of sulfuric acid. Then, the solution was heated under reflux for 5 hours. The resultant solution was poured into 2 l of water. The thus obtained viscous solid was washed with water and then dried. Thus, 28.3 g of a product comprising Compound (17) and its isomers was obtained. From the measurement by GPC, the oligomer content in the product was evaluated to be 7.2%.

SYNTHESIS EXAMPLE 5 [Synthesis of Compound (21)]

A product (21a) comprising Compound (21) was obtained in the same manner as in Synthesis Example 1, except that Compound (18) was used in place of Compound (1) as the starting material. The GPC measurement proved that the oligomer content in the product was 6.1%.

The reaction scheme for synthesizing Compound (21) is illustrated below.

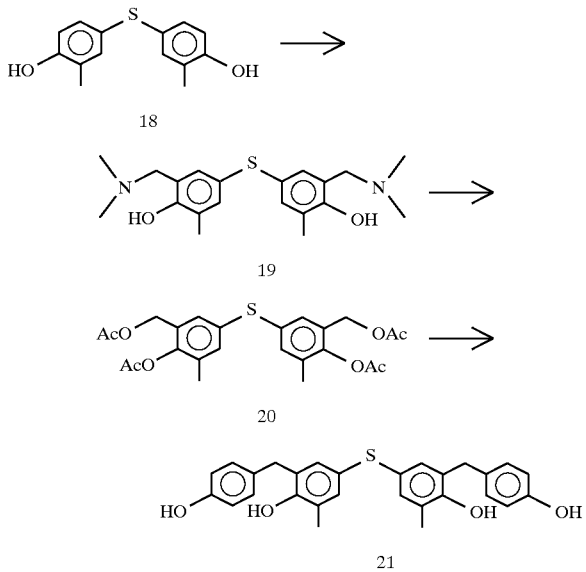

SYNTHESIS EXAMPLE 6 [Synthesis of Compound (25)]

Synthesis of Compound (25) was carried out in accordance with a reaction scheme illustrated below:

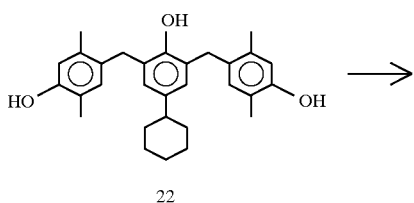

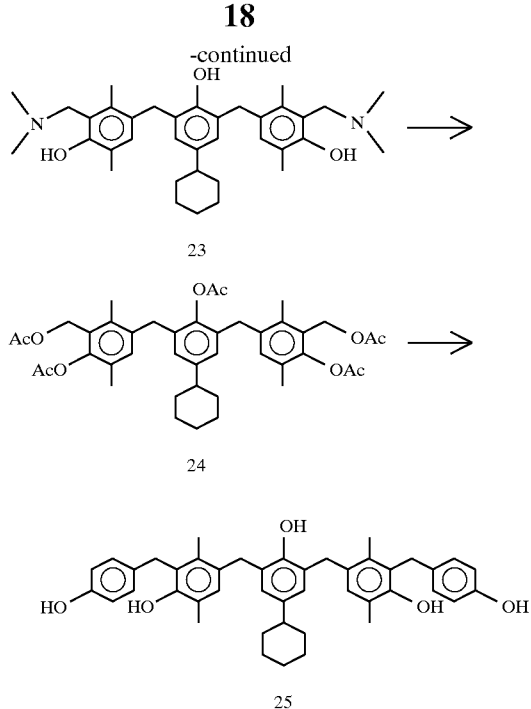

More specifically, 111.4 g of Compound (22), 900 g of a 50% aqueous solution of dimethylamine and 1 l of ethanol were put together, and homogenized by stirring. Thereto, 810 g of a 37% aqueous solution of formaldehyde was added dropwise over one hour, and then stirred for 10 hours under reflux. After the completion of the reaction, the white solid deposited was filtered off. Thus, 140 g of an aminomethylated compound (23) was obtained.

140 g of the aminomethylated compound (23) was put together with 1 kg of acetic andhydride, and heated at 150° C. with stirring. After the stirring was continued for 15 hours, excess acetic anhydride was distilled away under reduced pressure. The residue was dissolved in acetone, and then admixed with 1 l of distilled water to precipitate a white solid therefrom. The white solid precipitate was filtered off to give 175 g of an acetoxylated compound (24).

175 g of the obtained acetoxylated compound (24), 500 ml of methanol and 25 g of concentrated sulfuric acid were charged together, and stirred for 10 hours under a reflux condition. Further, 25 g of concentrated sulfuric acid was added thereto, and the stirring was continued for additional 10 hours. After the completion of the reaction, the resulting solution was poured into 10 l of distilled water, followed by washing with 5 l of distilled water. Thus, a product (25a) comprising Compound (25) and its isomers was obtained in a quantity of 160 g. The GPC measurement proved that the oligomer content in the product was 9.2%.

SYNTHESIS EXAMPLE 7 [Synthesis of Compound (28)]

Synthesis of Compound (28) was carried out in accordance with a reaction scheme illustrated below:

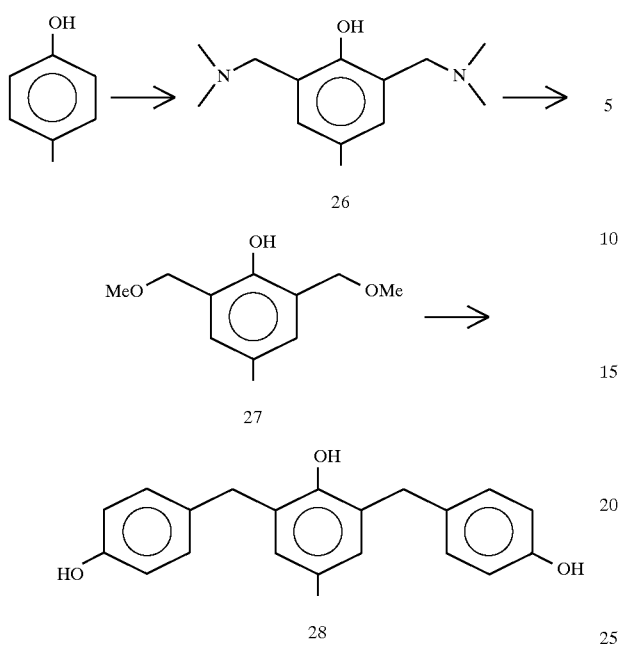

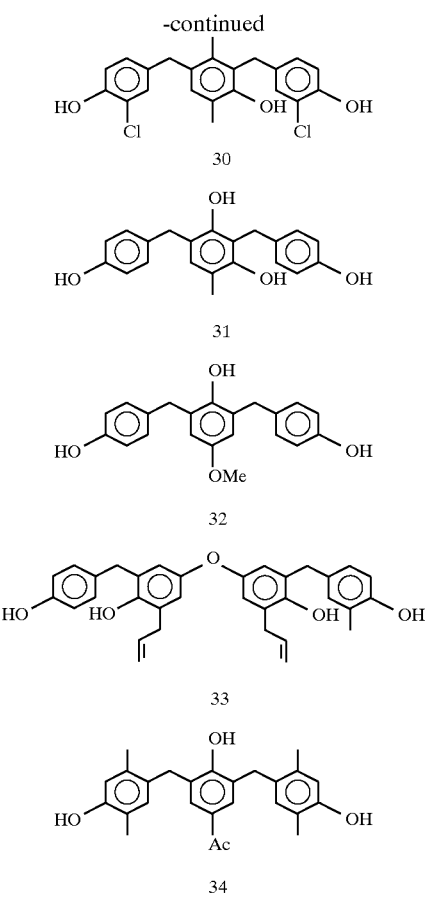

More specifically, 20 g of cresol, 167 g of a 50% aqueous solution of dimethylamine and 146 g of a 37% aqueous solution of formaldehyde were dissolved in 300 ml of ethanol, and heated for 5 hours under reflux. The resultant solution was poured into 2 l of water, and the viscous matter obtained was washed with water and then dried. Thus, 40.1 g of Compound (26) was obtained.

40.0 g of Compound (26) was dissolved in 1 l of dimethyl sulfoxide. Thereto, 53.6 g of methyl iodide was added dropwise over 30 minutes. The reaction was conducted for 2 hours at room temperature. To this reaction solution was added 29.2 g of sodium methoxide to undergo the reaction for 2 hours at 80° C. in a stream of nitrogen. The resultant solution was poured into 2 l of water, and rendered weakly acidic with hydrochloric acid. The thus obtained oily matter was washed with water and then dried to give 32.0 g of Compound (27).

30.0 g of Compound (27) and 290 g of phenol were dissolved in 500 ml of methanol, and thereto was added 1.5 g of sulfuric acid. Then, the solution was heated for 5 hours under reflux. The resultant solution was poured into 3 l of water. The thus obtained viscous solid was washed with water and then dried. Thus, 43.3 g of a product comprising Compound (28) and its isomers was obtained. The GPC measurement proved that the oligomer content in the product was 8.5%.

SYNTHESIS EXAMPLE 8

Compounds (29) to (34) illustrated below were obtained in the same method as adopted in Synthesis Example 1:

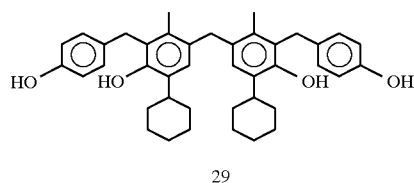

SYNTHESIS EXAMPLE 9 (Comparison)

A product (4b) comprising Compound (4) and its isomers was obtained using the same method as adopted in JP-A-63-83035, except that Compound (1) was used as the starting material. The GPC measurement proved that the oligomer content in the product was 14.3%.

SYNTHESIS EXAMPLE 10 (Comparison)

A product (9b) comprising Compound (9) and its isomers was obtained using the same method as adopted in JP-A-63-83035, except that Compound (6) was used as the starting material. The GPC measurement proved that the oligomer content in the product was 16.8%.

SYNTHESIS EXAMPLE 11 (Comparison)

A product (21b) comprising Compound (21) and its isomers was obtained using the same method as adopted in JP-A-63-83035, except that Compound (18) was used as the starting material. The GPC measurement proved that the oligomer content in the product was 33.1%.

SYNTHESIS EXAMPLE 12 (Comparison)

A product (25b) comprising Compound (25) and its isomers was obtained using the same method as adopted in JP-A-63-83035, except that Compound (22) was used as the starting material. The GPC measurement proved that the oligomer content in the product was 24.8%.

SYNTHESIS EXAMPLE A
Synthesis of Photosensitive Material (a)

In 200 ml of acetone were dissolved 20.0 g of the product (4a) obtained in Synthesis Example 1 and 24.4 g of 1,2-naphthoquinonediazido-5-sulfonyl chloride. Thereto, 10 ml of acetone solution containing 9.46 g of N-methylpiperidine was added dropwise at room temperature over 30 minutes, and then the reaction was conducted for 3 hours. The reaction mixture obtained was admixed with 5.7 g of acetic acid, and then poured into 1.5 l of water. As a result, a yellow precipitate separated out. The precipitate was filtered off, washed with water, and then dried. Thus, 39.7 g of 1,2-naphthoquinonediazido-5-sulfonic acid ester of Compound (4) (Photosensitive Material a) was obtained.

SYNTHESIS EXAMPLE B
Synthesis of Photosensitive Material (b)

In 200 ml of acetone, 23 g of the product (21a) obtained in Synthesis Example 5 and 27.0 g of 1,2-naphthoquinonediazido-5-sulfonyl chloride were dissolved. Thereto, a solution containing 10.4 g of N-methylpiperidine in 10 ml of acetone was added dropwise at room temperature over 30 minutes, and then the reaction was conducted for 3 hours. The reaction mixture obtained was admixed with 6.3 g of acetic acid, and then poured into 1.5 l of water. As a result, a yellow precipitate separated out. The precipitate was filtered off, washed with water, and then dried. Thus, 41.2 g of 1,2-naphthoquinonediazido-5-sulfonic acid ester of Compound (21) (Photosensitive Compound b) was obtained.

SYNTHESIS EXAMPLE C
Synthesis of Photosensitive Material (c)

In 120 ml of acetone, 9.82 g of the product (25a) obtained in Synthesis Example 6 and 8.03 g of 1,2-naphthoquinonediazido-5-sulfonyl chloride were dissolved. Thereto, a solution containing 3.1 g of N-methylpiperidine in 10 ml of acetone was added dropwise at room temperature over 30 minutes, and then the reaction was conducted for 3 hours. The reaction mixture obtained was admixed with 1.8 g of acetic acid, and then poured into 1 l of water. As a result, a yellow precipitate separated out. The precipitate was filtered off, washed with water, and then dried. Thus, 15.7 g of 1,2-naphthoquinonediazido-5-sulfonic acid ester of Compound (25) (Photosensitive Material c) was obtained.

SYNTHESIS EXAMPLE D (COMPARISON)

A photosensitive material (d) was obtained in the same manner as in Synthesis Example A, except that the product (4b) obtained in Synthesis Example 9 was used in place of the product (4a).

SYNTHESIS EXAMPLE E (COMPARISON)

A photosensitive material (e) was obtained in the same manner as in Synthesis Example B, except that the product (21b) obtained in Synthesis Example 11 was used in place of the product (21a).

SYNTHESIS EXAMPLE F (COMPARISON)

A photosensitive material (f) was obtained in the same manner as in Synthesis Example C, except that the product (25b) obtained in Synthesis Example 12 was used in place of the product (25a).

EXAMPLES 1 TO 3 a) Synthesis of Novolak Resin

A novolak resin (Resin N) was synthesized in the following manner: 30 g of p-cresol, 14 g of o-cresol, 35 g of 2,3-dimethylphenol, 15 g of 2,3,5-trimethylphenol and 6 g of 2,6-dimethylphenol were mixed with 50 g of diethylene glycol monomethyl ether, and placed in a three necked flask equipped with a stirrer, a reflux condenser and a thermometer. Thereto, 85 g of a 37% aqueous solution of formaldehyde was added, and stirred while the flask was heated with an oil bath kept at 110° C. At the time when the inside temperature rose to 90° C., 6.3 g of oxalic acid dihydrate was added. Further, the reaction was continued for 18 hours while the temperature of the oil bath was maintained at 130° C. Then, the reflux condenser was removed from the flask, and unreacted monomers was distilled away at 200° C. under reduced pressure. The thus obtained novolak resin (Resin N) had a weight average molecular weight of 3280 (reduced to a polystyrene basis) and a dispersibility of 2.75.

b) Preparation and Evaluation of Positive Working Photoresist Compositions:

A photosensitive material chosen from Photosensitive Materials (a), (b) and (c) obtained in the aforementioned Synthesis Examples (A), (B) and (C) respectively, Resin N obtained hereinabove, a solvent (methyl 3-methoxypropionate) and α,α,α'-tris(4-hydroxyphenyl)-1-ethyl-4-isopropylbenzene (Polyphenol Compound (P)) were mixed in proportions (by weight) set forth in Table 1, homogenized to make a solution, and then filtered through a Teflon filter having a pore diameter of 0.10 μm. In this manner, three photoresist compositions were prepared. Each photoresist composition was coated on a silicon wafer with a spinner adjusting the number of revolution to obtain a predetermined thickness, and then dried at 90° C. for 60 seconds by means of a vacuum contact hot plate, thereby obtaining a resist film having a thickness of 0.97 μm.

Each resist film was exposed to light by means of a reducing projection exposure apparatus (Model NSR-2005i9C, made by Nikon Corporation), underwent PEB at 110° C. for 60 seconds, developed for 1 minute with a 2.38% of aqueous solution of tetramethylammonium hydroxide, washed with water for 30 seconds, and then dried.

Each resist pattern thus obtained on the silicon wafer was observed under a scanning electron microscope, and thereby the resist performance was evaluated. In the evaluation, the resolution was expressed in terms of the threshold resolution under the exposure for reproducing a 0.60 μm mask pattern, and the depth of focus was expressed in terms of the focus range in which a 0.40 μm line-and-space pattern was resolved without a decrease in film thickness under the exposure for reproducing the 0.60 μm mask pattern.

COMPARATIVE EXAMPLES 1 TO 3

Photoresist compositions were prepared in the same manner as in Examples 1 to 3 respectively, except that Photosensitive Materials (d) to (f) obtained in Synthesis Examples D to F were used in place of Photosensitive Materials (a) to (c), respectively, and evaluated by the same method as in Examples 1 to 3.

The obtained results are shown in Table 1.

TABLE 1

|  | Amount of Novolak Resin added | Photosensitive Material species | Photosensitive Material amount added | Amount of Polyphenol Compound (P) added | Amount of Solvent added | Resolution ($\mu$m) | Depth of Focus ($\mu$m) |
| --- | --- | --- | --- | --- | --- | --- | --- |
| Example 1 | 80 | (a) | 60 | 20 | 400 | 0.30 | 1.8 |
| Example 2 | 80 | (b) | 62 | 20 | 360 | 0.30 | 1.7 |
| Example 3 | 70 | (c) | 55 | 30 | 380 | 0.28 | 2.2 |
| Comparative Example 1 | 80 | (d) | 60 | 20 | 400 | 0.32 | 1.5 |
| Comparative Example 2 | 80 | (e) | 62 | 20 | 360 | 0.34 | 1.0 |
| Comparative Example 3 | 70 | (f) | 55 | 30 | 380 | 0.30 | 1.8 |

As can be seen from Table 1, the positive working photoresist compositions using as the photosensitive material the naphthoquinonediazidosulfonic acid esters of polyphenol compounds obtained according to the method of the present invention were superior in resolution and depth of focus.

EXAMPLE 4 TO 6

Photosensitive Material (b) obtained in the foregoing Synthesis Example B, Resin N (the same novolak resin as used in Examples 1 to 3), a solvent (methyl 3-methoxypropionate), and the polyphenol compound of the present invention (the product (4a), (9a) or (25a) obtained in Synthesis Example 1, 2 or 6), were mixed in proportions (by weight) set forth in Table 2, homogenized to make a solution, and then filtered through a Teflon filter having a pore diameter of 0.10 $\mu$m. In this manner, three photoresist compositions were prepared. Each photoresist composition was coated on a silicon wafer with a spinner adjusting the number of revolution to obtain a predetermined thickness, and then dried at 90° C. for 60 seconds by means of a vacuum contact hot plate, thereby obtaining a resist film having a thickness of 0.97 $\mu$m.

Each resist film thus obtained was exposed to light by means of a reducing projection exposure apparatus (Model NSR-2005i9C, made by Nikon Corporation), underwent PEB at 110° C. for 60 seconds, developed for 1 minute with a 2.38% of aqueous solution of tetramethylammonium hydroxide, washed with water for 30 seconds, and then dried.

Each resist pattern thus obtained on the silicon wafer was observed under a scanning electron microscope, and thereby the resist performance was evaluated.

With respect to the evaluation results shown in Table 3, the sensitivity is defined as the reciprocal of the exposure amount required for reproducing a 0.60 $\mu$m mask pattern, and the sensitivity values shown in Table 3 are relative values, with the resist of Comparative Example 4 being taken as 1.0. As for the resolution, the threshold resolution under the exposure for reproducing a 0.60 $\mu$m mask pattern is set forth. The resist pattern shape is represented by an angle ($\theta$) which the resist wall in the vertical section of a 0.60 $\mu$m resist pattern forms with the silicon wafer plane.

The development latitude is represented by a change in line width of a 0.60 $\mu$m resist pattern which is caused when the style of developing is changed from a paddle method to a shower method although the same exposure was given. The criteria were as follows.

A: Change was hardly observed.
B: Some change was observed.
C: Considerable change was observed.

The development residue (scum) is represented by the extent of scum generated when a 0.40 $\mu$m resist pattern is formed. The criteria were as follows.

A: No scum was observed.
B: A small amount of scum was observed.
C: A considerable amount of scum was observed.

COMPARATIVE EXAMPLES 4 TO 6

Photoresist compositions were prepared in the same manner as in Examples 4 to 6 except that the products (4b), (9b) and (25b) obtained in Synthesis Examples 9, 10 and 12 were used as the polyphenol compounds in place of the products (4a), (9a) and (25a), respectively, as shown in Table 2 below, and evaluated in the same manner as in Examples 4 to 6.

Evaluation results thus obtained are shown in Table 3.

TABLE 2

|  | Amount of Resin added | Amount of Photo-Sensitive Material added | Polyphenol Compound species | Polyphenol Compound Amount added | Amount of Solvent added |
| --- | --- | --- | --- | --- | --- |
| Example 4 | 75 | 48 | (4a) | 25 | 400 |
| Example 5 | 80 | 60 | (9a) | 20 | 380 |
| Example 6 | 70 | 52 | (25a) | 30 | 350 |
| Comparative Example 4 | 75 | 48 | (4b) | 25 | 400 |
| Comparative Example 5 | 80 | 60 | (9b) | 20 | 380 |
| Comparative Example 6 | 70 | 52 | (25b) | 30 | 350 |

TABLE 3

|  | Relative Sensitivity | Resolution ($\mu$m) | Resist Pattern Shape ($\theta$) | Development Latitude | Development Residue |
| --- | --- | --- | --- | --- | --- |
| Example 4 | 1.2 | 0.30 | 89 | A | A |
| Example 5 | 1.3 | 0.32 | 88 | A | A |
| Example 6 | 1.3 | 0.30 | 89 | A | A |
| Comparative Example 4 | 1.0 | 0.33 | 87 | B | B |
| Comparative Example 5 | 1.2 | 0.35 | 85 | C | C |
| Comparative Example 6 | 1.1 | 0.32 | 87 | B | C |

As can be seen from Table 3, the resists to which the polyphenol compounds obtained by the method of the present invention had been added were superior in all of the sensitivity, resolution, resist pattern shape and developability (well balanced among resist characteristics). In particular, they were reduced in development residue and had higher resolution.

According to the synthesis method of the present invention, a high pure polyphenol compound with less generation of by-products such as oligomer can be obtained with ease and in high yield.

By using the polyphenol compound obtained by the above method, a positive photoresist composition having high sensitivity, resolution and developability, especially high resolution, can be provided.

While the invention has been described in detail with reference to specific embodiments, it will be apparent to one skilled in the art that various changes and modifications can be made to the invention without departing from its spirit and scope.

What is claimed is:

1. A positive working photoresist composition comprising an alkali-soluble resin and 1,2-naphthoquinonediazido-5- and/or -4-sulfonic acid ester of the polyphenol product obtained by a method of synthesizing a polyphenol product, comprising (i) introducing at least one —CHRNR'R" group onto aromatic ring(s) of a phenol compound having from one to ten aromatic ring(s), wherein R represents a hydrogen atom, an alkyl group which may contain a hetero atom, a cycloalkyl group which may contain a hetero atom, an aralkyl group which may contain a hetero atom, or an aryl group, and R' and R", which may be the same or different, each represents an alkyl group which may contain a hetero atom, a cycloalkyl group which may contain a hetero atom, an aralkyl group which may contain a hetero atom, or an aryl group, and R' and R" may combine with each other to form a ring, (ii) converting the —CHRNR'R" group into a —CHRA group via one to three steps, wherein A represents a hydroxyl group, an alkoxy group, an acyloxy group, a halogen atom, a quaternary ammonium salt or a sulfonyloxy group, and (iii) condensing the thus converted phenol compound and a phenol compound.

2. A positive working photoresist composition comprising an alkali-soluble resin and a naphthoquinonediazide compound, further comprising the polyphenol product obtained by a method of synthesizing a polyphenol product, comprising (i) introducing at least one —CHRNR'R" group onto aromatic ring(s) of a phenol compound having from one to ten aromatic ring(s), wherein R represents a hydrogen atom, an alkyl group which may contain a hetero atom, a cycloalkyl group which may contain a hetero atom, an aralkyl group which may contain a hetero atom, or an aryl group, and R' and R", which may be the same or different, each represents an alkyl group which may contain a hetero atom, a cycloalkyl group which may contain a hetero atom, an aralkyl group which may contain a hetero atom, or an aryl group, and R' and R" may combine with each other to form a ring, (ii) converting the —CHRNR'R" group into a —CHRA group via one to three steps, wherein A represents a hydroxyl group, an alkoxy group, an acyloxy group, a halogen atom, a quaternary ammonium salt or a sulfonyloxy group, and (iii) condensing the thus converted phenol compound and a phenol compound.

* * * * *